United States Patent [19]

Pellico

[11] Patent Number: 5,453,284
[45] Date of Patent: * Sep. 26, 1995

[54] STABILIZED ENZYMATIC DENTIFRICE

[76] Inventor: Michael A. Pellico, 3024 Military Ave., Los Angeles, Calif. 90272

[*] Notice: The portion of the term of this patent subsequent to Aug. 9, 2011 has been disclaimed.

[21] Appl. No.: 283,816

[22] Filed: Aug. 1, 1994

Related U.S. Application Data

[63] Continuation-in-part of Ser. No. 10,841, Jan. 29, 1993, Pat. No. 5,336,494.

[51] Int. Cl.$^6$ .................................................. A61K 7/28
[52] U.S. Cl. .............................. 424/94.4; 424/49; 424/50; 424/94.1; 424/94.2
[58] Field of Search .................... 424/94.1–94.4, 424/49, 50

[56] References Cited

U.S. PATENT DOCUMENTS

| | | | |
|---|---|---|---|
| 4,150,113 | 4/1979 | Hoogendoorn | 424/50 |
| 4,178,362 | 12/1979 | Hoogendoorn | 424/48 |
| 4,269,822 | 5/1981 | Pellico | 424/50 |
| 4,537,764 | 8/1985 | Pellico | 424/50 |
| 4,564,519 | 1/1986 | Pellico | 424/48 |
| 4,576,817 | 3/1986 | Montgomery | 424/94 |
| 4,578,265 | 3/1986 | Pellico | 424/50 |
| 4,617,190 | 10/1986 | Montgomery | 426/61 |
| 5,176,899 | 1/1993 | Montgomery | 424/50 |

Primary Examiner—Phelan, D. Gabrielle
Attorney, Agent, or Firm—Donald Diamond

[57] ABSTRACT

Hydro-activated and/or oxygen activated aqueous, enzymatic, antimicrobial dentifrices are stabilized against enzymatic activation prior to oral application of the dentifrice by incorporating a thickener into the dentifrice formulation so as to provide the formulation with an enzyme immobilizing viscosity which inhibits enzymatic action during processing and in the dentifrice package. An illustrative, thickened, enzymatic dentifrice with this enhancement contains glucose oxidase, glucose, lactoperoxidase and potassium thiocyanate together with carboxymethylcellulose in an amount to provide the dentifrice with a viscosity of at least about 800 centipoises.

16 Claims, No Drawings

STABILIZED ENZYMATIC DENTIFRICE

REFERENCE TO RELATED APPLICATION

This application is a continuation-in-part of U.S. patent application Ser. No. 08/010,841 filed Jan. 29, 1993, now U.S. Pat. No. 5,336,494, and entitled Pet Chewable Products With Enzymatic Coating, the disclosure of which is incorporated herein by reference.

BACKGROUND OF THE INVENTION

1. Field of the Invention

This invention relates to enzymatic dentifrice compositions and, more particularly, to stabilized, aqueous, enzymatic dentifrices which, upon oral application, produce an anti-bacterial and bacteriostatic effect in the oral cavity by activation of the enzyme system within the dentifrice.

2. Related Art

It is disclosed in the prior art that enzymatic anti-bacterial systems, predicated on oxidoreductase enzymes such as glucose oxidase, can be incorporated into oral care products and other products such as powder milk (U.S. Pat. No. 4,617,190) and bandages (U.S. Pat. No. 4,576,817) for producing an anti-bacterial effect in a defined environment.

U.S. Pat. No. 4,150,113 (Hoogendoorn et al., 1979) and U.S. Pat. No. 4,178,362 (Hoogendoorn et al., 1979) disclose, respectively, an enzymatic toothpaste and an enzymatic chewable dentifrice containing glucose oxidase which acts on glucose present in saliva and tooth plaque to produce hydrogen peroxide. The patentees note that oral bacterial, through enzyme systems having SH-GROUPS, effect glycolysis of food products containing sugars and point out that lactoperoxidase, which is present in saliva, provides the means for transferring oxygen from hydrogen peroxide to the oral bacteria resulting in the oxidation of the SH-containing enzymes into inactive disulfide enzymes. It is further disclosed that the dentifrice may be formulated with potassium thiocyanate.

U.S. Pat. No. 4,269,822 (Pellico et al., 1981) discloses an antiseptic dentifrice containing an oxidizable amino acid substrate and an oxidoreductase enzyme specific to such substrate for producing hydrogen peroxide and ammonia upon oral application of the dentifrice, with pre-application stability being maintained by limiting the quantity of any water present in the dentifrice.

U.S. Pat. No. 4,537,764 (Pellico et al., 1985) discloses an enzymatic dentifrice containing Beta-D-Glucose and glucose oxidase for producing hydrogen peroxide upon oral application of the dentifrice, with pre-application stability being maintained by limiting any water in the dentifrice to not more than about 10 wt. % based on the weight of the dentifrice.

U.S. Pat. No. 4,578,365 (Pellico et al., 1986) discloses a di-enzymatic dentifrice which contains, for example, glucose and glucose oxidase for producing hydrogen peroxide upon oral application of the dentifrice and further contains a thiocyanate salt and lactoperoxidase for interacting with hydrogen peroxide to produce a hypothiocyanate (sic) with pre-application stability being maintained by limiting any water in the dentifrice to not more than about 10 wt. % based on the weight of the dentifrice.

U.S. Pat. No. 4,564,519 (Pellico et al., 1986) discloses a di-enzymatic chewable dentifrice which contains, for example, glucose and glucose oxidase for producing hydrogen peroxide upon chewing the dentifrice and further contains a thiocyanate salt and lactoperoxidase for interacting with hydrogen peroxide to produce a hypothiocyanate (sic) bacterial inhibitor, with pre-application stability being maintained by limiting any unbound water in the chewable dentifrice to an amount not more than about 1.0 wt. % and limiting the total water, bound and unbound, to not more than about 10 wt. %.

U.S. Pat. No. 5,176,899 (Montgomery, 1993) discloses an aqueous enzymatic dentifrice which contains, for example, Beta-D-Glucose and glucose oxidase for producing hydrogen peroxide upon oral application of the dentifrice and, optionally, contains a thiocyanate salt and lactoperoxidase for interacting with hydrogen peroxide to produce a hypothiocyanite (OSCN-) bacteriostatic agent, with pre-application stability being maintained by processing and packaging the dentifrice under vacuum conditions or in an inert gas environment so as to limit the level of dissolved oxygen in the dentifrice.

The enzymatic dentifrice compositions described in U.S. Pat. Nos. 4,564,519 and 4,578,265 comprise an enzyme system containing an oxidizable substrate and an oxidoreductase enzyme specific to such substrate for producing hydrogen peroxide upon oral application of the dentifrice with the chemical environment of the oral cavity providing the source of the additional reactant (oxygen) or reactants (oxygen, water) to effect the enzymatic reaction. It is disclosed in these patents that it is essential to limit any water present in the described dentifrices to an amount not more than about 10 wt. % in order to impart maximum stability and shelf life to the compositions since water promotes the oxidation/reduction reaction and is also a reactant in certain enzymatic reactions.

It would, of course, be advantageous to increase the water concentration of the aforesaid enzymatic dentifrice compositions to an amount in excess of 10 wt. % in order to improve the oral application characteristics of the dentifrice, without initiating the enzymatic reaction within the dentifrice package and thereby preserve the package integrity of the product.

SUMMARY OF THE INVENTION

In accordance with this invention, there is provided an aqueous enzymatic dentifrice having a water content in excess of 10 wt. % and containing, per gram of dentifrice, from about 0.015 to about 0.6 millimole of oxidizable substrate and from about 0.5 to about 5,000 International Units of oxidoreductase enzyme specific to such substrate for producing hydrogen peroxide upon oral application of the dentifrice, and further containing non-toxic, ambient, water soluble thickener in an amount to provide the dentifrice with a viscosity from about 800 to about 75,000 centipoises to thereby stabilize the dentifrice against the production of hydrogen peroxide prior to oral application of the dentifrice.

DETAILED DESCRIPTION

The invention described herein is directed to the use of thickener in aqueous dentifrice compositions containing a hydro-activated and/or oxygen activated enzyme system to thereby provide a viscosity which inhibits the enzymatic reaction prior to oral application of the dentifrice.

The thickeners which can be used in the practice of this invention comprise non-toxic, ambient, water soluble hydrocolloids such as carboxymethylcellulose (sodium carboxymethylcellulose), hydroxymethylcellulose, high-viscosity starch, hydrogenated starch, xanthan gum and mixture thereof as well as equivalents thereof. The thickener is generally present in an amount to provide the enzymatic dentifrice with a viscosity from about 800 to about 75,000 centipoises, with an intermediate amount being so selected as to provide the dentifrice with a viscosity from about 2,000 to about 60,000 centipoises, and a preferred amount being so selected as to provide the dentifrice with a viscosity from about 15,000 to about 50,000 centipoises. Viscosity determinations can be made by utilizing a suitable viscometer in accordance with applicable procedures well known in the art.

The enzymatic component of the dentifrice comprises a first enzyme system containing an oxidizable substrate and an oxidoreductase enzyme specific to such substrate for producing hydrogen peroxide upon oral application of the dentifrice, with the chemical environment of the oral cavity providing the source of additional reactant (oxygen) or reactants (oxygen, water) to effect the enzymatic reaction. Illustrative examples of oxidoreductase enzymes and their corresponding oxidizable substrates which can be used in the practice of this invention are set forth in the following table:

TABLE A

| OXIDOREDUCTASE ENZYME | OXIDIZABLE SUBSTRATE |
| --- | --- |
| Glucose Oxidase | B-D-glucose |
| Hexose Oxidase | Hexose |
| Galactose Oxidase | D-galactose |
| Pyranose Oxidase | Pyranose |
| Pyruvate Oxidase | Pyruvate |
| Oxalate Oxidase | Oxalate |
| DL-Aminoacid oxidase | DL-Aminoacid |

In an illustrative reaction, glucose oxidase catalyzes the interaction of beta-D-glucose, water and oxygen during the oral application of the dentifrice to produce hydrogen peroxide and gluconic acid.

Glucose oxidase is characterized in the literature as a glycoprotein containing two molecules of flavine-adenine dinucleotide which has a molecular weight of approximately 150,000, an isoelectric point at pH 4.2 and an optimum pH at 5.5 with a broad pH range from 4 through 7.

The oxidizable substrate is generally present in the dentifrice in an amount from about 0.015 to about 0.6 millimole per gram of dentifrice and, preferably, from about 0.025 to about 0.1 millimole per gram of dentifrice while the oxidoreductase enzyme specific to the substrate is generally present in the dentifrice in an amount from about 0.5 to about 5,000 International Units (hereinafter sometimes abbreviated IU) per gram of dentifrice and, preferably, from about 10 to about 1,000 IU per gram of dentifrice. The term millimole identifies that quantity in grams corresponding to the molecular weight of the composition divided by one thousand. The term International Unit(s) identifies that amount of enzyme that will effect catalysis of 1.0 micromole of substrate per unit at pH 7.0 and 25 C. Oxidoreductase enzymes are supplied in dry or liquid form with the label specifying the concentration in International Units on a per gram or per milliliter basis, as appropriate.

In addition to the first enzyme system comprising oxidizable substrate and oxidoreductase enzyme specific to such substrate for producing hydrogen peroxide, the enzymatic dentifrice of this invention is advantageously provided with a second enzyme system containing a peroxidatic peroxidase and an alkali metal salt of an oxygen accepting anion for interacting with hydrogen peroxide to produce an oxidized anionic bacterial inhibitor.

Peroxidases which can be used in the practice of this invention include lactoperoxidase, horse radish peroxidase, iodide peroxidase, chloride peroxidase and myeloperoxidase. Oxidizable salts which can be used in the practice of this invention include, for example, the thiocyanate, chloride or iodide salt of sodium, potassium, ammonium, calcium or magnesium or mixtures of such salts. In the presence of hydrogen peroxide, the oxygen accepting anions of the aforesaid salts, namely, thiocyanate, chloride and iodide are oxidized to hypothiocyanite, hypochlorite and hypoiodite, respectively.

The peroxidase is generally present in the dentifrice in an amount from about 0.1 to about 10,000 International Units per gram of dentifrice and, preferably, from about 10 to about 1,500 International Units per gram of dentifrice while the oxidizable salt is generally present in the dentifrice in an amount from about 0.0001 to about 0.01 millimole per gram of dentifrice and, preferably, from about 0.001 to about 0.006 millimole per gram of dentifrice.

The operable integrity of the enzymatic system can be affected by catalase which is present in commercial glucose oxidase as well as mucous membrane tissue. Catalase, which is extraneous to the enzymatic system of this invention, competes with peroxidatic peroxidase for hydrogen peroxide. In order to reduce loss of hydrogen peroxide through the presence of catalase, an effective amount of an enzymatic inhibitor specific to catalase can be advantageously incorporated into the enzymatic solution. An ascorbic salt such as sodium ascorbate, potassium ascorbate, ascorbyl palmitate, or mixtures thereof can be used as an enzymatic inhibitor which is specific to catalase. An effective amount of ascorbate salt for catalase inhibition is from about 0.000001 to about 0.0001 millimole per gram of dentifrice. Iron salts such as ferrous sulphate can be incorporated into the enzymatic dentifrice as potentiator for ascorbate salt in its role as catalase inhibitor.

The enzymatic dentifrice of this invention may advantageously be formulated with an aminohexose as, for example, an aminoglucose such as glucosamine, N-actyl glucosamine or mixtures thereof in order to increase the yield or accumulation of oxidized anionic bacterial inhibitor. The aminoglucose is generally present in the enzymatic dentifrice in an amount from about 0.0001 to about 0.002 millimole per gram of dentifrice and, preferably, in an amount from about 0.003 to about 0.001 millimole per gram of dentifrice.

As a result of the increase in viscosity of the enzymatic dentifrice provided by the thickener, the dentifrice can be formulated with water in excess of 10 wt. % without initiating an enzymatic reaction prior to oral application of the dentifrice. Water is generally present in the enzymatic dentifrice in an amount from about 10 wt. % to about 60 wt. %, with an intermediate amount being from about 20 to about 50 wt. % and a preferred amount being from about 25 to about 35 wt. %.

Dentifrices, especially toothpaste, are preferred oral compositions for the purpose of this invention. In addition to the thickener, enzyme system and water, the dentifrice compositions of this invention may contain typical formulating ingredients for enzymatic toothpaste such as humectants, buffering agents, abrasives, surfactants, fluorides, flavors, colors, and sweeteners as well as a variety of auxiliary dentifrice components, as more particularly identified and described in the above-identified patents, the disclosures of which are incorporated herein by reference, together with the limitations as specified therein.

The enzymatic dentifrice, in the form of a toothpaste, can be prepared in any suitable manner as, for example, by blending the dry ingredients into the liquid ingredients, with agitation, until a smooth mixture is obtained, with the proviso that shear sensitive ingredients, which include the enzymes, are added last to minimize shear impact on such ingredients.

Adjunct antibacterial agents such as the enzyme lysozyme and the protein lactoferrin can also be added to the enzymatic formulations of this invention.

In contrast to the prior art as illustrated by U.S. Pat. Nos. 4,537,764 and 4,578,265, and in accordance with this invention, it has now been found that oxidoreductase enzyme stability can be maintained in an aqueous dentifrice that contains well in excess of 10 wt. % water, as shown by the example hereinafter set forth, when a thickener is used in the aqueous dentifrice so as to provide a viscosity of at least 800 centipoises.

EXAMPLE I

This example illustrates an aqueous enzymatic toothpaste containing 30 wt. % water together with an enzyme system containing Beta-D-glucose, glucose oxidase, lactoperoxidase and potassium thiocyanate.

| Composition | Weight, Grams |
| --- | --- |
| Water | 30.0 |
| Glycerine | 38.0 |
| Carboxymethylcellulose | 6.0 |
| Silica | 15.0 |
| Sodium methyl cocyl taurate | 2.0 |
| Titanium dioxide | 8.0 |
| Lactoperoxidase (100 IU/mg) | 0.0005 (50 IU) |
| Beta-D-glucose | 1.0 |
| Glucose oxidase (100 IU/mg) | 0.001 (100 IU) |
| Potassium thiocyanate | 0.150 |
| Flavor | Q.S. |

The viscosity of this aqueous, enzymatic toothpaste is 30,000 centipoises and the toothpaste has an enzymatic shelf life in excess of 2 years.

EXAMPLE II

This example illustrates an aqueous enzymatic toothpaste containing 25 wt. % water together with an enzyme system containing Beta-D-glucose, glucose oxidase,

| Composition | Weight, Grams |
| --- | --- |
| Water | 25.0 |
| Glycerine | 23.0 |
| Sorbitol | 25.0 |
| Carboxymethylcellulose | 3.0 |
| Xanthan gum | 4.0 |
| Sodium lauryl sarcosinate | 2.0 |
| Silica | 17.0 |
| Beta-D-glucose | 1.0 |
| Lactoperoxidase (100 IU/mg) | 0.0005 (50 IU) |
| Glucose oxidase (100 IU/mg) | 0.001 (100 IU) |
| Potassium thiocyanate | 0.150 |
| Flavor | Q.S. |

The viscosity of this aqueous, enzymatic toothpaste is 40,000 centipoises and the toothpaste has an enzymatic shelf life in excess of 3 years.

EXAMPLE III

This example illustrates an aqueous enzymatic toothpaste containing 53 wt. % water together with an enzyme system containing hexose, hexose oxidase, myeloperoxidase and potassium thiocyanate.

| Composition | Weight, Grams |
| --- | --- |
| Water | 53.0 |
| Sorbitol | 10.0 |
| Hydrogenated starch | 5.0 |
| Pluronic P84 | 2.0 |
| Silica | 10.0 |
| Calcium pyrophosphate | 12.0 |
| Hexose | 7.0 |
| Hexose oxidase (100 IU/mg) | 0.0001 (10 IU) |
| Myeloperoxidase (100 IU/mg) | 0.0002 (20 IU) |
| Potassium thiocyanate | 0.150 |
| Flavor | Q.S. |

The viscosity of this aqueous, enzymatic toothpaste is 2,000 centipoises and the toothpaste has an enzymatic shelf life in excess of 2 years.

EXAMPLE IV

This example illustrates an aqueous enzymatic toothpaste containing 57 wt. % water together with an enzyme system containing Beta-D-glucose, glucose oxidase, myeloperoxidase and potassium thiocyanate.

| Composition | Weight, Grams |
| --- | --- |
| Water | 57.0 |
| Sorbitol | 10.0 |
| High viscosity starch | 10.0 |
| Silica | 4.0 |
| Sodium lauryl sarcosinate | 3.0 |
| Dicalcium phosphate | 10.0 |
| Beta-D-glucose | 5.0 |
| Glucose oxidase (100 IU/mg) | 0.005 (500 IU) |
| Myeloperoxidase (100 IU/mg) | 0.001 (100 IU) |
| Potassium thiocyanate | 0.150 |
| Sodium fluoride | 0.76 |
| Flavor | Q.S. |

The viscosity of this aqueous, enzymatic toothpaste is 3,000 centipoises.

EXAMPLE V

This example illustrates an aqueous, clear gel toothpaste containing 45 wt. % water together with an enzyme system containing beta-D-glucose, glucose oxidase, lactoperoxidase and potassium iodide.

| Composition | Weight, Grams |
| --- | --- |
| Water | 45.0 |
| Sorbitol | 15.0 |
| Glycerine | 6.0 |
| Xylitol | 5.0 |
| Silica | 20.0 |
| Hydroxymethylcellulose | 4.0 |

-continued

| Composition | Weight, Grams |
|---|---|
| Sodium lauryl sarcosinate | 3.0 |
| Beta-D-glucose | 2.0 |
| Glucose oxidase (100 IU/mg) | 0.05 (5,000 IU) |
| Lactoperoxidase (100 IU/mg) | 0.008 (800 IU) |
| Potassium iodide | 0.09 |
| Color | Q.S. |
| Flavor | Q.S. |

The viscosity of this aqueous, enzymatic gel toothpaste is 60,000 centipoises and the toothpaste has an enzymatic shelf life in excess of 3 years.

In view of the foregoing descriptions and examples, it will become apparent to those of ordinary skill in the art that equivalent modifications thereof may be made without departing from the spirit and scope of this invention.

That which is claimed is:

1. An aqueous, enzymatic dentifrice having a water content in excess of 10 wt. % and containing, per gram of dentifrice, from about 0.015 to about 0.6 millimole of oxidizable substrate and from about 0.5 to about 5,000 International Units of oxidoreuctase enzyme specific to such substrate for producing hydrogen peroxide upon oral application of the dentifrice; and further containing non-toxic, ambient, water soluble thickener in an amount to provide the dentifrice with a viscosity from about 800 to about 75,000 centipoises to thereby stabilize the dentifrice against the production of hydrogen peroxide prior to oral application of the dentifrice.

2. The dentifrice of claim 1 wherein the amount of water soluble thickener is so selected as to provide the dentifrice with a viscosity from about 2,000 to about 60,000 centipoises.

3. The dentifrice of claim 1 wherein the amount of water soluble thickener is so selected as to provide the dentifrice with a viscosity from about 15,000 to about 50,000 centipoises.

4. The dentifrice of claim 1 wherein the upper limit of the water content is about 60 wt. %.

5. The dentifrice of claim 1 wherein the water content is from about 20 to about 50 wt. %.

6. The dentifrice of claim 1 wherein the water content is from about 25 to about 35 wt. %.

7. The dentifrice of claim 1 wherein the water soluble thickener comprises hydrophillic colloid.

8. The dentifrice of claim 1 wherein the water soluble thickener is a member selected from the group consisting of carboxymethylcellulose, hydroxymethylcellulose, high viscosity starch, hydrogenated starch, xanthan gum and mixtures thereof.

9. The dentifrice of claim 1 wherein the oxidizable substrate is beta-D-Gluclose and the oxidoreductase enzyme is gluclose oxidase.

10. The dentifrice of claim 1 wherein the oxidizable substrate is hexose and the oxidoreductase enzyme is hexose oxidase.

11. The dentifrice of claim 1 wherein the oxidizable substrate is present in an amount from about 0.025 to about 0.1 millimole per gram of dentifrice and the oxidoreductase enzyme specific to the substrate is present in an amount from about 10 to 1,000 International Units per gram of dentifrice.

12. The dentifrice of claim 1 which further contains an effective amount of an augmenting anti-bacterial agent selected from the group consisting of lysozyme, lactoferrin and mixtures thereof.

13. The dentifrice of claim 1 which also contains, per gram of dentifrice, from about 0.1 to about 10,000 International Units of peroxidatic peroxidase selected from the group consisting of lactoperoxidase, horse radish peroxidase, iodide peroxidase, chloride peroxidase, myeloperoxidase and mixtures thereof and from about 0.0001 to about 0.01 millimole of an alkali metal salt of an oxygen accepting anion selected from the group consisting of thiocyanate, chloride and iodide or a mixture of such salts for interacting with hydrogen peroxide to produce oxidized anionic bacetrial inhibitor.

14. The dentifrice of claim 13 where the peroxidase is present in an amount from about 10 to about 1,500 International Units per gram of dentifrice and the oxidizable salt is present in an amount from about 0.001 to about 0.006 millimole per gram of dentifrice.

15. The dentifrice of claim 13 wherein the peroxidase is lactoperoxidase and the alkali metal salt is alkali metal thiocyanate.

16. The dentifrice of claim 13 wherein the oxidizable substrate is beta-D-gluclose, the oxidoreductase enzyme is gluclose oxidase, the peroxidase is lactoperoxidase, the oxidizable salt is potassium thiocyanate and the thickener is carboxymethyl cellulose.

* * * * *